(12) United States Patent
Hamou et al.

(10) Patent No.: US 8,834,463 B2
(45) Date of Patent: Sep. 16, 2014

(54) MEDICAL RESECTOR

(75) Inventors: Jacques Hamou, Paris (FR); Markus Simmen, Schwerzenbach (CH); Otmar Stillhard, Steckborn (CH)

(73) Assignee: Karl Storz GmbH & Co. KG (DE)

( * ) Notice: Subject to any disclaimer, the term of this patent is extended or adjusted under 35 U.S.C. 154(b) by 994 days.

(21) Appl. No.: 12/885,134

(22) Filed: Sep. 17, 2010

(65) Prior Publication Data
US 2011/0066149 A1    Mar. 17, 2011

(30) Foreign Application Priority Data
Sep. 17, 2009 (DE) .......................... 10 2009 041 602

(51) Int. Cl.
   *A61B 18/14*    (2006.01)
   *A61B 17/32*    (2006.01)
   *A61B 18/18*    (2006.01)

(52) U.S. Cl.
   CPC ..... *A61B 18/1485* (2013.01); *A61B 2018/1407* (2013.01); *A61B 219/2269* (2013.01); *A61B 2018/1861* (2013.01); *A61B 17/32002* (2013.01)
   USPC .............................................. 606/41; 606/45

(58) Field of Classification Search
   USPC ................... 606/41, 45, 46; 600/105
   See application file for complete search history.

(56) References Cited

U.S. PATENT DOCUMENTS

| 4,116,198 A * | 9/1978 | Roos ................................ 606/46 |
| 5,133,713 A | 7/1992 | Huang et al. |
| 5,857,962 A * | 1/1999 | Bracci et al. ................... 600/105 |
| 5,902,300 A * | 5/1999 | Hahnen et al. .................. 606/46 |
| 5,938,661 A * | 8/1999 | Hahnen ............................ 606/46 |
| 6,032,673 A | 3/2000 | Savage et al. |
| 7,815,639 B2 * | 10/2010 | Brommersma ................. 606/46 |
| 8,109,958 B1 * | 2/2012 | Alleyne ......................... 606/170 |
| 2002/0183589 A1 * | 12/2002 | Brommersma et al. ...... 600/105 |
| 2003/0144661 A1 * | 7/2003 | Brommersma et al. ........ 606/46 |
| 2003/0149442 A1 * | 8/2003 | Gellman et al. .............. 606/170 |
| 2004/0044343 A1 * | 3/2004 | Brommersma et al. ........ 606/46 |
| 2005/0171531 A1 * | 8/2005 | Eliachar et al. ................. 606/46 |
| 2005/0228403 A1 * | 10/2005 | Ho et al. ........................ 606/113 |
| 2006/0015007 A1 * | 1/2006 | Aue et al. ...................... 600/105 |
| 2008/0188711 A1 * | 8/2008 | Eliachar et al. ............... 600/106 |

FOREIGN PATENT DOCUMENTS

| DE | 1759256 U | 1/1958 |
| DE | 3313325 A1 | 10/1984 |
| DE | 9420821 U1 | 4/1995 |
| DE | 69824851 T2 | 7/2005 |
| DE | 102006039696 A1 | 2/2008 |
| EP | 0448857 A1 | 10/1991 |
| WO | 9316755 A1 | 9/1993 |
| WO | 2006048199 A1 | 5/2006 |

OTHER PUBLICATIONS

European Search Report; Application No. EP 10009171; Feb. 23, 2011; 5 pages.

* cited by examiner

*Primary Examiner* — Linda Dvorak
*Assistant Examiner* — Jocelyn D Ram
(74) *Attorney, Agent, or Firm* — St. Onge Steward Johnston & Reens LLC

(57) ABSTRACT

A medical resector for oblating, cutting, or coagulating human or animal tissue includes a rotatable high-frequency electrode on the distal end of a shaft of the medical resector and an axle that runs from the proximal end to the distal end of the shaft and is mechanically coupled with the high-frequency electrode on the distal end. The axle is positioned on the distal end of the shaft in the center or as close as possible to the center of the cross-section of the shaft and on the proximal end of the shaft on the border or as close as possible to the border of the cross-section of the shaft.

16 Claims, 3 Drawing Sheets

MEDICAL RESECTOR

CROSS-REFERENCE TO RELATED APPLICATIONS

The present application claims priority of German patent application No. 10 2009 041 602.1 filed on Sep. 17, 2009, the content of which is incorporated herein by reference.

FIELD OF THE INVENTION

The present invention relates to a resector for medical applications having a rotatable high-frequency electrode.

BACKGROUND OF THE INVENTION

In high-frequency surgery (HF surgery) an electrode supplied with high-frequency electric current is used for sectioning tissue. A high-frequency electrode made of a wire sling is used, for instance, for detaching tissue. The sling is pushed or pulled through the tissue by the operator in order to cut out snippets or shavings of tissue of just about any length.

A medical resector as set forth in the following description can be combined with an endoscope to form a resectoscope, in such a way that a shaft of the endoscope is positioned inside a channel in the shaft of the medical resector.

A medical resector developed by Jacques Hamou comprises a rotating wire sling as high-frequency electrode. The wire sling ablates the tissue in the form of small shavings or snippets, for instance similarly to the functioning of a milling head for machined processing of workpieces. Medical resectors of this type are described for instance in WO 2006/048199 A1 and DE 10 2006 039 696 A1. Resection or ablation or the detaching of tissue in small fragments makes possible an immediate visual control, simplified handling, and clean and precise ablation of tissue. In addition, the small portions of tissue are easily removable, for instance by suction integrated in the medical resector.

As with all instruments used for microinvasive medical interventions, the smallest possible shaft diameter is also desirable for a medical resector. The shaft of a medical resector as a rule comprises a channel for inserting the shaft of an endoscope. The ablation of tissue can be directly observed through the endoscope by means of the medical resector. In addition, the shaft of a medical resector with a rotatable high-frequency electrode comprises an axle for transmitting the rotation motion from a drive mechanism to the rotatable high-frequency electrode. As a result of the smallest possible cross-section of the shaft of the medical resector, the axle is situated close to the endoscope or to the channel for the endoscope. In addition, the rotatable HF electrode should not extend above the contour of the shaft of the medical resector, in order to make possible, for example, the insertion by means of a trocar. To make it possible, with the given diameter of the shaft of the medical resector, to simultaneously have a maximum diameter of the HF electrode, the axle must be located as close as possible to the symmetrical axis of the shaft. However, this leads to geometric problems at the proximal end in coupling the medical resector and a drive mechanism for rotating the rotatable HF electrode.

Additional problems with conventional medical resectors with rotatable HF electrodes are the irrigation of the work area and the removal of severed pieces of tissue from said work area. Irrigation and the removal of severed tissue pieces are necessary to ensure a clear view of the work area, for example through the aforementioned endoscope.

Other problems that are often not resolved, or not sufficiently resolved, with conventional medical resectors with rotatable HF electrode are the protection of patients from injury from the rotatable HF electrode and the protection of a rotatable HF electrode from damage, in particular during insertion and positioning of the medical resector in the work area in a cavity in the patient's body.

It is an object of the present invention to create an improved medical resector.

SUMMARY OF THE INVENTION

This object is achieved through a medical resector for ablating, cutting, or coagulating human or animal tissue, with: a rotatable high-frequency electrode on the distal end of a shaft of the medical resector; an axle, which runs from the proximal end to the distal end of the shaft and is mechanically coupled on the distal end with the high-frequency electrode, wherein the axle is positioned on the distal end of the shaft in the center or as close as possible to the center of the cross-section of the shaft and on the proximal end of the shaft on the border or as close as possible to the border of the cross-section of the shaft. Refinements are indicated in the subsidiary claims.

Embodiments of the present invention are based on the idea, in a medical resector for ablating, cutting, or coagulating human or animal tissue, with a rotatable HF electrode at the distal end of a shaft and with an axle that runs from the proximal end to the distal end of the shaft and is coupled on the distal end with the HF electrode, to position the axle on the distal end of the shaft in the center or as close as possible to the center of the cross-section of the shaft and on the proximal end of the shaft on or as close as possible to the edge of the cross-section of the shaft.

The axle can be rigid or flexible. A rigid axle comprises a single straight axis of rotation. A flexible axle comprises at every site a local axis of rotation, so that the length and direction of the axis of rotation vary along the flexible axle.

The axis of rotation runs in particular in such a way that the distance of the axis of rotation from the center of the shaft of the medical resector decreases monotonously or strictly monotonously from the proximal end to the distal end of the shaft. In particular, both the axle and the shaft of the medical resector are straight, whereas the axis of rotation of the axle is positioned non-parallel to the longitudinal axis of the shaft. This non-parallelism represents, in particular, a departure from parallelism that exceeds both the precision customary in medical technology and the tolerances customary in medical technology. In particular, between the longitudinal axis of the medical resector or of its shaft on the one hand and the axis of rotation of the axle there is an angle of at least 0.4 degrees, in particular an angle between 0.6 and 1.0 degrees. The longitudinal axis of the medical resector is, in particular, the longitudinal axis of the shaft of the medical resector. In the event of a rigid straight shaft, the longitudinal axis of the shaft is the straight line on which the centerpoints of the cross-sectional surfaces of the shaft lie.

The medical resector is, for example, a hystero-ablator or a uro-ablator.

This non-parallelism or angle between the axis of rotation of the axle and the longitudinal axis of the shaft of the medical resector makes possible at the same time a central or almost central positioning of the rotatable HF electrode on the distal end on the one hand, and an eccentric positioning of the end of the axle and of the coupling device positioned on it on the proximal end of the medical resector on the other hand.

The central positioning of the rotatable HF electrode on the distal end of the shaft can, among other reasons, be advantageous because the HF electrode can thus have a maximum diameter without extending above the contour of the shaft of the medical resector. The eccentric positioning of the axle and of the coupling device on the proximal end allows, in particular, a maximum distance for instance from a shaft of an endoscope that can be inserted into the shaft of the medical resector and thus maximum construction space for a drive mechanism and the coupling of the medical resector with the drive mechanism.

A central positioning of the rotatable HF electrode on the distal end of the shaft of the medical resector is understood to mean the most central arrangement possible under the given conditions. This exactly central positioning is possible only under certain conditions. For instance, if a spatial area, in particular an isolated channel, is provided in the shaft of the resector for inserting a shaft of an endoscope, the axis of rotation of the axle can lie in the center of the shaft of the medical resector only if the center of the shaft is not within the channel or too close to its edge. Here the size of the channel is determined primarily by the diameter of the endoscope that is to be inserted into the channel. Therefore the axis of rotation of the axle can lie in the center of the shaft only if the sum of the diameter of the endoscope, of the radius of the axle, and of the thickness of a partition between endoscope and axle, if applicable, is smaller than the inner radius of the shaft of the medical resector.

Otherwise the distance between the axis of rotation of the axle on the one hand and the center of the cross-section of the shaft of the medical resector on the other hand is at least the difference between the sum of the diameter of the shaft of the endoscope, of the radius of the axle, and, if applicable, of the thickness of the partition between the endoscope and axle on the one hand and the inner radius of the shaft of the medical resector on the other hand. In addition, it is essential to ensure that to minimize friction in inserting the endoscope in the channel provided for it in the shaft of the medical resector, the lumen of this channel must be somewhat larger than the cross-section of the endoscope. In the event of a non-circular cross-section of the shaft of the medical resector or a non-circular cross-section of the shaft of the endoscope, corresponding adjustments apply.

On the proximal end of the shaft of the medical resector, the axle is in particular positioned on the edge of the cross-section of the shaft. The axle can be positioned on the proximal end of the shaft only close enough to the edge of the cross-section so that it does not touch it but instead maintains the distance necessary for minimizing friction in rotating. The necessary distance of the axle from the edge of the cross-section of the shaft is, if applicable, enlarged by the wall thickness of a guide tube or a bearing for the axle. The distance of the axis of rotation of the axle from the edge of the lumen of the shaft of the medical resector basically can exceed the sum of the radius of the axle and, if applicable, of the wall thickness of a guide tube of the axle or of a bearing for the axle only by the size of the distance required to minimize friction in the rotation of the axle. In other words, in order to achieve, on the proximal end of the medical resector, a maximum distance of the axle from an endoscope inserted in the shaft of the medical resector, the axle on the proximal end of the shaft is positioned in particular immediately contiguous to the inner surface of the shaft of the medical resector or is separated from it only by a bearing or the wall of a guide tube.

If a medical resector, as described above, comprises a shaft with a cylindrical mantle surface, the rotatable HF electrode can include a wire loop or can consist of a wire loop whose center, area midpoint, or axis of rotation is situated on or at least as close as possible to the axis of symmetry of the mantle surface of the shaft. This arrangement is again restricted in the aforementioned manner by the diameter or radii of the shaft of the medical resector, shaft of the endoscope, and axle. An arrangement of the area midpoint of the wire loop on the axis of symmetry or as close as possible to the axis of symmetry of the mantle surface of the shaft makes possible a maximum diameter of the rotatable HF electrode without any protrusion above the contour of the shaft of the medical resector. In particular, in this case the diameter of the rotatable HF electrode can be as large or nearly as large as the outer diameter of the shaft of the medical resector.

A medical resector as described above can include a drive mechanism or can be configured for use with a drive mechanism that provides a rotary frequency in a rotary frequency range that is included in a range of 10 revolutions per minute up to 200 rpm.

To ascertain appropriate rotary frequencies or rotary figures or rotation frequencies, theoretical reflections and calculations were first employed that were based on empirical values with conventional, non-rotating sling-shaped HF electrodes. For such rotating sling-shaped HF electrodes, depending on the tissue and other circumstances of the individual case, a cutting speed of approximately 10 millimeters per second can be considered to have proven itself. It is assumed that the cutting speed shall not exceed the proven cutting speed of 10 mm per second at any spot on the rotating HF electrode.

The cutting speed is also linearly dependent on the radius as well as on the rotary frequency. At a maximum cutting speed of 10 mm per second and at a diameter of the wire sling or of the HF electrode of 4 mm, computations result in a rotary frequency of 48 revolutions per minute, and at 6 mm a rotary frequency of 32 rpm and at 8 mm a rotary frequency of 24 rpm. Extensive, detailed, and therefore also time-consuming experimental investigations by Jacques Hamou confirm that at the usual diameters of HF electrodes or of wire slings at rotary frequencies between 30 rpm and 60 rpm, major advantages are realized, surprisingly not only with respect to the cutting capacity and the cutting quality. Depending on the size and shape of the HF electrode as well as on the tissues to be cut, lower rotary frequencies from about 10 rpm or 20 rpm and higher rotary frequencies up to about 100 rpm, or in an individual case up to 150 rpm or 200 rpm, are advantageous.

Surprisingly, at the aforementioned rotary frequencies, in particular at rotary frequencies between 30 rpm and 60 rpm, an optimum is achieved with respect to the ablation capacity on the one hand and the observability and controllability of ablation on the other hand. Despite a favorable ablation capacity, the ablated tissue pieces are so small that they interfere only slightly with the view of the work area through an endoscope positioned, for instance, in the medical resector. The slight negative impact on the view through the endoscope is also based on the fact that the tissue pieces can be suctioned out and thus removed from the field of vision quickly and without the risk of clogging the medical resector.

Surprisingly, the rotary frequency of the rotatable HF electrode also plays an important role in the impact on medical personnel and thus in turn indirectly in the quality of the achieved result. At the aforementioned rotary frequencies, especially at rotary frequencies up to 60 rpm, the movement of the HF electrode can still be perceived by the eye of medical personnel without difficulty and halted. Observation of the HF electrode is therefore not yet perceived as stressful. Every individual ablated tissue piece and the resulting exposed deeper tissue layers and their surfaces can be pursued or observed. At clearly higher rotary frequencies above 100 rpm and higher, at more than 200 rpm, the movement of the HF electrode and of the tissue pieces and their observation prove increasingly tiring. This is hazardous for medical applications not only involving the medical personnel but also, above all, for the patient.

In addition, at the aforementioned rotary frequencies, in particular in the range of 30 rpm to 60 rpm, the ablation can be especially well controlled. The described good observability on the one hand and the sufficiently rapid but not too rapid ablation are apparently especially suited for control and regulation of the ablation by medical personnel.

The aforementioned advantages are achieved thus and, especially also in this combination, at no other rotary frequency. Lower rotary frequencies result in an insufficient ablation capacity. In addition, the individual ablated tissue fragments are too large to be suctioned off perfectly. Moreover, the tissue fragments cover the exposed tissue layers too long before they are completely detached and removed, for instance by suction, from the field of vision.

At higher rotary frequencies above 200 rpm, depending on the tissue, often even at rotary frequencies over 100 rpm or over 60 rpm, the quality of the cuts, in particular the coagulation, is often insufficient. In addition, the observation of the rapid movements is tiring for the eye of medical personnel. Depending on the tissue, in addition, the ablated tissue pieces can be too small so that they cling in particular to surfaces and can be suctioned off only with difficulty.

Embodiments of the present invention are based on the idea of configuring a funnel collar for application to a distal end of a shaft of a medical resector with a rotatable HF electrode for ablating, cutting, or coagulating human or animal tissue in such a manner that it partially surrounds the rotatable HF electrode when it is positioned on the distal end of the shaft of the medical resector. To surround the rotatable HF electrode or the spatial area occupied by it, in mantle form in parts, the funnel collar extends, especially distally, beyond the end of the shaft of the medical resector. The funnel collar can thus, in many cases, protect the rotatable HF electrode from undesired touching and a patient from injury by the rotatable HF electrode.

In particular, the funnel collar has the shape of a segment of a cylindrical mantle. The shape of the funnel collar here can correspond essentially to the mantle surface of the shaft of the medical resector, for which the funnel collar is foreseen and configured. The funnel collar can be configured so as to be partially contiguous with the mantle surface of the shaft of the medical resector and to be bolted, cemented, catch-locked, welded, or soldered with it or connected with it by clamping or by means of a clip, which in particular is integrated into the funnel collar. The funnel collar can thus be configured in such a way that it does not widen, or does not significantly widen, the contour of the shaft of the medical resector. Its use with a conventional trocar can therefore be maintained.

In particular, a proximal border area of the funnel collar overlaps with a distal border area of the wall of the shaft forming the mantle surface.

In the area of the overlap the funnel collar can be positioned outside the wall of the shaft. An advantage of this arrangement can consist in the fact that the HF electrode can be configured to be exactly as large as without the funnel collar. Alternatively the funnel collar in the area of the overlap can be positioned inside the wall of the shaft. As a result the funnel collar is guaranteed to lie completely within the contour of the shaft. The medical resector can thus be usable, for instance, with a trocar, with which a corresponding medical resector without the funnel collar can also be used.

Whether the funnel collar is positioned outside or inside the wall of the shaft, said shaft wall can have a simple geometric structure, which can be produced with minor expense. In particular, the funnel collar can be positioned on the outside or inside of the wall of a conventional shaft that protrudes distally in collar shape and with constant wall thickness. Alternatively, the wall of the shaft can have a reduced wall thickness in the area of the overlap with the funnel collar. The funnel collar can also have a reduced wall thickness in the area of the overlap.

An additional advantage of the funnel collar is that it can be configured to divert fluid emerging at the distal end of the shaft of the medical resector and thus to improve the irrigation of the work area. The improved irrigation can lead to improved removal of tissue pieces ablated by a medical resector and thus an improved view of the processed tissue and of the processed tissue surface.

In addition, the funnel collar on a medical resector can effect an improvement in the suction of ablated tissue pieces through the shaft of the medical resector. For the same reason, there can be improvement in the removal of the ablated tissue pieces and in the view of the work area.

To achieve the aforementioned advantages concerning flushing and suction, the funnel collar can be configured to surround at least halfway the HF electrode with respect to the longitudinal axis of the shaft of the medical resector. In particular, the funnel collar here is configured to surround the HF electrode by at most three-quarters with respect to the longitudinal axis of the shaft. An angle of approximately 250 degrees has proven especially effective.

A funnel collar as described above can, in addition, be configured in such a way that in arranging the funnel collar on the distal end of the shaft of a medical resector, the distal end of the HF electrode of the medical resector extends beyond a distal edge of the funnel collar or both end flush with one another. Alternatively, the funnel collar can be configured so that in arranging the funnel collar on the distal end of the shaft of a medical resector the distal edge of the funnel collar extends beyond a distal end of the HF electrode of the medical resector.

The three aforementioned configurations can be advantageous for various applications. The longer the funnel collar is and the farther it extends beyond the HF electrode, the better it protects it from undesired contact and damage and the patient from injury by the HF electrode. The shorter the funnel collar is configured and the farther the HF electrode extends beyond the funnel collar, the better the medical resector can be used to also process surfaces that are perpendicular to the longitudinal axis of the shaft of the medical resector.

The funnel collar, in addition, can assume the function of a guide in the ablation of tissue. For example, the medical resector is guided in such a way that the distal edge of the funnel collar is contiguous with the surface that has not yet been ablated or the surface newly formed by the ablation of tissue. Both of these make possible a good guidance of the thickness of the ablated layer. The thickness of the ablated layer here can depend on the protrusion of the rotatable HF electrode beyond the distal edge of the funnel collar or on the protrusion of the distal edge of the funnel collar beyond the rotatable HF electrode as well as on the angle between the shaft of the medical resector and the surface that is to be processed or has been processed.

For many applications a configuration has been advantageous in which the distal end of the HF electrode and the distal edge of the funnel collar terminate flush with one another; that is, they lie in a plane that is essentially perpendicular to the longitudinal axis of the shaft of the medical resector.

To avoid impeding the effect of the HF capacity transmitted via the HF electrode to the human or animal tissue, in particular the cutting, ablating and/or coagulating effect, the funnel collar can consist of polyetheretherketone (PEEK), another synthetic, ceramic, or another electrically insulating material.

A medical resector as described above can include a funnel collar as described. In addition, a medical resector as previously described can be combined with an endoscope to form a resectoscope, so that a shaft of the endoscope is positioned in a channel in the shaft of the medical resector.

Embodiments of the present invention are based on the idea of providing on the distal end of a medical resector a suction opening that is inclined with respect to the longitudinal axis of the shaft of the medical resector.

The suction opening comprises a border that can lie in a plane or in a tilted surface. The surface of the suction opening hereinafter is understood to mean that surface in which the border of the suction opening lies, and whose entire interfaces are straight, perpendicular to the longitudinal axis of the shaft of the medical resector. The suction opening inclines toward the longitudinal axis of the shaft of the medical resector by the same distance as the central or centered perpendicular line of the surface of the suction opening is not parallel to the longitudinal axis of the shaft of the medical resector.

In particular, the angle between the central surface vertical line of the surface of the suction opening and the longitudinal axis of the shaft of the medical resector is at least 75 degrees. Angles between 45 and 75 degrees have proven especially appropriate.

The suction opening in particular is configured in such a way that all surface perpendicular lines of the surface of the suction opening form an angle of at least 30 degrees with the longitudinal angle of the shaft of the medical resector.

The aforementioned inclination of the suction opening can support and improve effective suction of an unclear or soiled fluid and/or of tissue pieces from the vicinity of the distal end of the medical resector. Suction is particularly improved by the fact that the inclined suction opening can be greater than a suction opening can be that is directed parallel to the longitudinal axis of the shaft of the medical resector. In addition, suction can be improved by the fact that on the distal end of the medical resector—in particular, on the edge of a distal end of an endoscope or around the distal end of the endoscope—discharged flushing fluid is suctioned out through the incline of the outlet opening, not immediately but only after larger-scale mixing with the impurities and/or tissue pieces that are to be suctioned out. This can require rapid, thorough clearing of the fluid in a cavity in which the medical resector is operating.

Embodiments of the present invention are based on the idea of providing a funnel collar and a suction opening on the distal end of a medical resector, where one section of the border of the suction opening forms a constant continuation of a section of the border of the funnel collar.

In particular, one section of the border of the suction opening forms a constant continuation of a section of the border of the funnel collar if one end of the section of the border of the suction opening and one end of the section of the border of the funnel collar are at a distance that is not greater than a wall thickness of the funnel collar or not greater than a wall thickness of the shaft of the medical resector or not greater than the sum of the wall thickness of the funnel collar and the wall thickness of the shaft of the medical resector.

In particular, one section of the border of the suction opening forms a constant continuation of a section of the border of the funnel collar if the two sections on opposite facing ends of the section of the border of the suction opening and of the border of the funnel collar are in directions that differ by less than 30 degrees or by less than 10 degrees.

For example, the suction opening comprises an essentially D-shaped border with a straight section and an arched section. The straight section of the border of the suction opening is positioned perpendicular to the longitudinal axis of the shaft of the medical resector. The aforementioned sections of the border of the funnel collar lying opposite to one another are close to the aforementioned corners of the border of the suction opening, in particular essentially parallel. The aforementioned sections of the border of the funnel collar lying opposite to one another are close to the aforementioned corners of the border of the suction opening, in particular in each case essentially parallel to the particular neighboring end of the arched section of the border of the suction opening.

The configuration and arrangement of the suction opening in such a way that one section of the border of the suction opening forms a constant continuation of a section of the border of the funnel collar, can make possible an especially good suction in case of a shortage of space. In particular, it can make possible a suction opening that is especially large and/or especially close to the suction opening that reaches as far as the funnel collar. Consequently this configuration and arrangement of the suction opening simultaneously make possible a good channeling of a flushing fluid through the funnel collar and an effective suction of flushing fluid, although on the distal end of the medical resector—in particular on the border of a distal end of an endoscope or around the distal end of the endoscope—flushing fluid is suctioned out, not immediately for the most part, but only after large-scale mixing with substances that are to be removed through the suction opening. This can enhance rapid and thorough clearing of the fluid in a cavity in which the medical resector is inserted.

With the aforementioned suction opening, the funnel collar can be configured in such a way, and the medical resector in the foreseen application can be conducted in such a manner, that ablated tissue pieces and other impurities that interfere with the view are directed to the suction opening and effectively removed by the sections of the border of the funnel collar that are opposite the processed surface.

A medical resector with a suction opening, which is inclined with respect to the longitudinal axis of the shaft of the medical resector and/or whose border comprises a section that forms a constant continuation of a section of the border of a funnel collar, can include an axle whose axis of rotation is parallel or, as described above, not parallel to the longitudinal axis of the shaft of the medical resector.

BRIEF DESCRIPTION OF THE DRAWINGS

In the following, embodiments are described with reference to the appended illustrations, which are as follows.

DETAILED DESCRIPTION OF THE INVENTION

Figure 1:
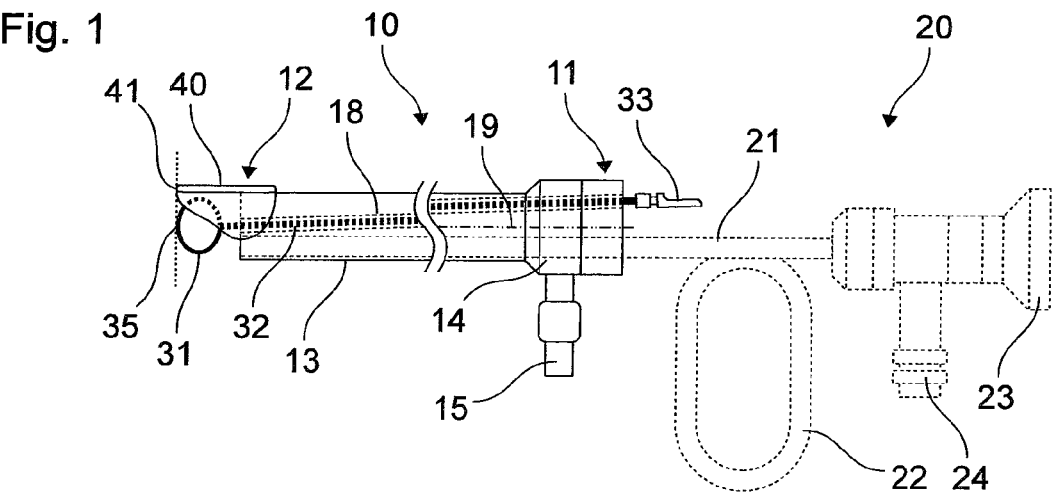
FIG. 1 shows a schematic depiction of a medical resector.

FIG. 1 shows a schematic depiction of a medical resector 10 having a proximal end 11, a distal end 12, and a shaft 13 that extends from the proximal end 11 to the distal end 12. The shaft 13 is cylindrical, with a circular, elliptical, oval, or any other cross-section. The longitudinal axis 19 of the shaft 13 is parallel to the plane of projection of FIG. 1. Because the longitudinal axis 19 runs close to the distal end 12 of the resector 10 in the area of other devices shown in FIG. 1, it is shown as close to only the proximal end 11 of the medical resector 10 in order to avoid confusion in the illustration. In fact the longitudinal axis 19 runs along the entire medical resector 10.

On its proximal end 11 the medical resector comprises a drain chamber 14 having a connection 15 for a suction device that is not shown in FIG. 1. An endoscope 20 or its shaft 21 can be inserted into the drain chamber 14 and the shaft 13. In addition the medical resector 10 can comprise a corresponding channel with openings on both ends, which extends through the drain chamber 14 and the shaft 13 from the proximal end 11 to the distal end 12 of the medical resector. In addition the medical resector 10 includes a guide tube 18 and/or two or more bearings for an axle 32 that is described hereafter. The medical resector 10 is also usable without the endoscope 20. The endoscope 20 is therefore illustrated with broken lines.

The endoscope 20 includes the aforementioned shaft 21, a grip 22 that improves the manual operation of the endoscope 20 or another handle, an eyepiece 23, and a coupling 24 for connecting the endoscope 20 with a light source that is not shown in FIG. 1. Alternatively the grip 22 or another handle differing from that shown in FIG. 1 is positioned on a shaft, into which the shaft 21 of the endoscope can be inserted and, in particular, can be fastened or locked there. The endoscope 20 can be guided independently of the medical resector 10, for instance by being rotated in the medical resector 10, with the grip 22 or another handle on the endoscope 20 or alternatively on a shaft in which the shaft 21 of the endoscope 20 is guided and held.

The medical resector 10 also includes a rotatable HF electrode 31 on its distal end 12. The rotatable HF electrode 31 is affixed on an axle 32 or is configured as forming a single piece with it. The axle 32 extends on the interior of the shaft 13 of the medical resector 10 from the rotatable HF electrode 31 on the distal end 12 to a coupling 33 on the proximal end 11 in the guide tube 18 of the medical resector and/or in two or more bearings that are not shown in FIG. 1. The coupling 33 is positioned proximal to the drain chamber 14. The axle 32 is configured to transmit a rotation of the coupling 33 to the HF electrode 31.

The axle 32 and thus also the axis of rotation of the rotatable HF electrode 31, of the axle 32, and of the coupling device 33 are not parallel to the longitudinal axis 19 of the shaft 13. The axis of rotation and the longitudinal axis 19 form an angle of at least 0.4 degree, in particular an angle between 0.6 and 1.0 degree or an angle of essentially 0.8 degree. This angle makes possible, on the one hand, a central positioning of the HF electrode 31 on the distal end 12 and, on the other hand, a maximum distance between the coupling device 33 on the proximal end 11 and the shaft 21 of the endoscope 20.

Positioned on the distal end 12 is an optional funnel collar 40 consisting of polyetheretherketone, plastic, ceramic, or another electrically insulating material. The funnel collar 40 protects the HF electrode 31 from undesired contact and damage and protects the human or animal body from injury from the HF electrode 31, in particular during insertion of the medical resector 10.

In addition the funnel collar 40 can direct a fluid exiting on the distal end 12 of the medical resector 10. In addition or alternatively, the funnel collar 40 can channel or concentrate a suction effect generated on the distal end 12 of the medical resector 10 onto the spatial area around the HF electrode 31. In either case, the funnel collar 40 improves the view through the endoscope 20 of a surface that has been processed by means of the rotatable HF electrode 31.

A drive mechanism, not shown in FIG. 1, for the rotatable HF electrode 31 can be coupled with the medical resector 10 described above with reference to FIG. 1. The drive mechanism is configured in particular as a drive unit that, without the need for an additional drive unit, provides a rotation frequency in a rotation frequency range between 10 revolutions per minute (rpm) and 200 rpm.

A broken line perpendicular to the longitudinal axis 19 of the shaft 13 of the medical resector 10 on the distal end 35 of the rotatable HF electrode 31 and on the distal edge 41 of the funnel collar 40 indicates that both lie essentially in a plane that is perpendicular to the longitudinal axis 19 of the shaft 13 of the medical resector 10.

Figure 2:
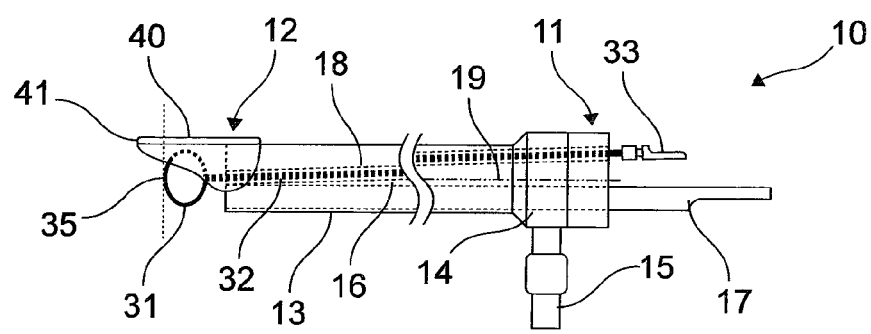
FIG. 2 shows a schematic depiction of an additional medical resector.
Figure 3:
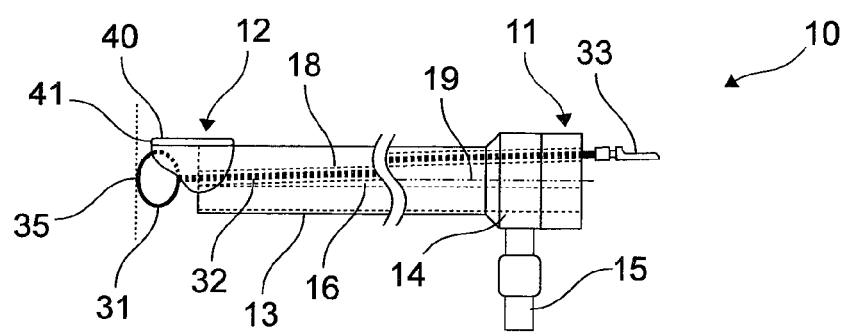
FIG. 3 shows a schematic depiction of an additional medical resector.

The depictions in FIGS. 2 and 3 correspond largely to the depiction in FIG. 1, although in each case no endoscope is positioned in the medical resector 10. Contrary to the configuration shown in FIG. 1, the medical resector 10 illustrated in FIG. 2 comprises a funnel collar 40, whose distal edge 41 extends beyond the distal end 35 of the rotatable HF electrode 31 and whose proximal end 42 overlaps with the shaft 13 of the resector 10. In comparison with the configuration from FIG. 1, this can cause improved protection of the rotatable HF electrode 31 from damage from undesired contact and improved protection of a patient from injury from the rotatable HF electrode 31.

In the configuration shown in FIG. 3, the distal end 35 of the rotatable HF electrode 31 extends beyond the distal edge 41 of the funnel collar 40. In comparison with the configurations described above with reference to FIGS. 1 and 2, this configuration can facilitate a processing of surfaces that are perpendicular or essentially perpendicular to the longitudinal axis 19 of the shaft 13 of the medical resector 10.

The medical resectors 10 displayed in FIGS. 2 and 3 differ further from the one described above with reference to FIG. 1 through a partition 16, which divides the interior space of the shaft 13 of the medical resector 10 into a first lumen and a second lumen. The first lumen is provided to position a shaft of an endoscope therein and/or to direct a flushing fluid to the distal end 12 of the shaft 13. The second lumen is provided to suction out tissue fragments severed by means of the rotatable HF electrode. The partition, as shown in FIGS. 2 and 3, can be tubular in shape or can have the cross-section described hereafter with reference to FIGS. 4A-4B.

The medical resector 10 illustrated in FIG. 2 distinguishes itself in addition from the ones described above with reference to FIGS. 1 and 3 in that a guide tube 17 is provided proximal to the drain chamber 14. The guide tube 17, in the proximal direction, lengthens the first lumen, which is separated by the partition 16. The shaft 21 of an endoscope 20, as already described above with reference to FIG. 1, can be inserted in the guide tube 17 and in the first lumen, separated by the partition 16, as far as the distal end 12 of the medical resector 10. The aforementioned drive mechanism, not shown in FIGS. 1 through 3, can in addition be supported and/or fastened on the guide tube 17.

Figure 4A:
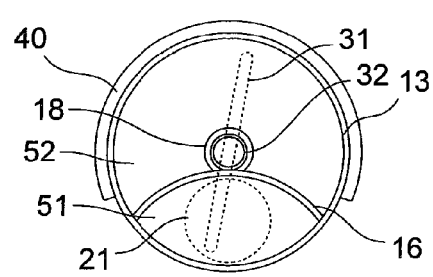
FIG. 4A shows a schematic depiction of a distal end of a shaft of a medical resector.
Figure 4B:
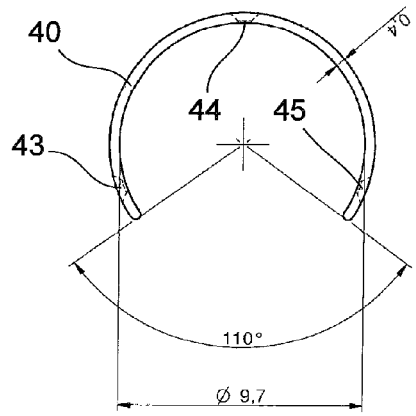
FIG. 4B shows a schematic depiction of a funnel collar adapted to be positioned on a distal end of a shaft of a medical resector.

FIG. 4A shows a schematic overhead view of a distal end of a shaft of a medical resector, as it was described above with reference to FIGS. 1 through 3. FIG. 4B shows a schematic overhead view of a funnel collar that can be positioned on the distal end of the shaft of the medical resector. The plane of projection in each case is perpendicular to the longitudinal axis 19 of the shaft 13.

It can be recognized in FIG. 4A that the partition 16 divides the interior of the shaft 13 of the medical resector into a first lumen 51 and a second lumen 52. In the first lumen 51 a rinsing liquid can be guided to the distal end of the shaft 13 and can exit there. Alternatively or in addition, the shaft 21 of an endoscope 20 can be positioned in the first lumen 51, as described above with reference to FIG. 1.

The axle 32 is positioned in the second lumen 52 in a guide tube 18 or in corresponding bearings. In addition, liquid, gaseous, or solid material can be suctioned from the distal end of the shaft 13 via the second lumen 52. In particular, tissue fragments ablated by the rotatable HF electrode 31 can thereby be removed from the work area.

It can also be recognized in FIG. 4 that the funnel collar 40 encloses the shaft 13 and the rotatable HF electrode 31 more than halfway, with reference to the longitudinal axis 19 of the shaft 13, but in this case by about two-thirds.

It can also be recognized in FIGS. 4A and 4B that the funnel collar 40 encloses the shaft 13 and the rotatable HF electrode 31 more than halfway, with reference to the longitudinal axis 19 of the shaft 13, but in this case by about two-thirds.

Shown in FIG. 4B is a funnel collar 40 that differs in a few details from the funnel collar illustrated in FIG. 4A. In particular, a few dimensions are indicated by way of example with the funnel collar 40 illustrated in FIG. 4B. It can be recognized, among other things, that the funnel collar 40 shown in FIG. 4B is configured to encompass a shaft 13 and a rotatable HF electrode 31 within a total angle of approximately 250 degrees.

In addition, the funnel collar shown at right in FIG. 4B comprises three attachment openings 43, 44, 45. Each of these fastening apertures 43, 44, 45 is configured as a clearance hole with a partly conical shape for inserting a countersunk screw. The funnel collar 40 can be fastened on the distal end 12 of a shaft 13 of a medical resector by means of three countersunk screws in the three fastening apertures. Alternatively the funnel collar 40 can be fastened on the distal end 12 of a shaft 13 of a medical resector by means of a different number of countersunk or other types of screws and/or by cementing, welding, soldering, catch-locking, or by clamping.

Figure 5:
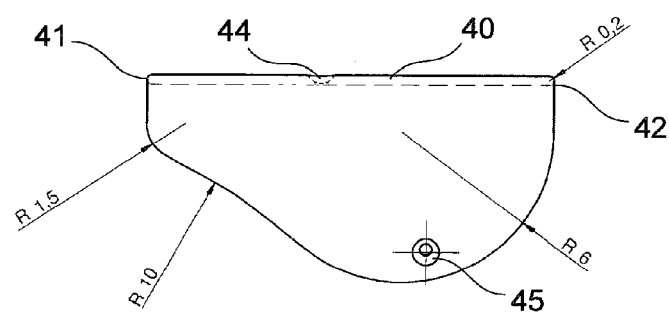
FIG. 5 shows a schematic depiction of the funnel collar from FIG. 4.
Figure 6:
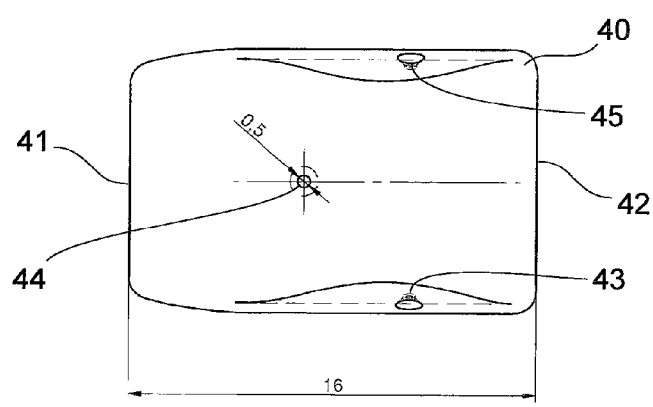
FIG. 6 shows a schematic depiction of the funnel collar from FIG. 4.

FIGS. 5 and 6 show additional views of the funnel collar 40 presented in FIG. 4B. FIG. 5 shows a side view, wherein the plane of projection of FIG. 5 is parallel to the longitudinal axis 19 of the shaft 13 of the medical resector 10 and corresponds to the planes of projection of FIGS. 1 through 3. FIG. 6 shows a view from below, wherein the plane of projection is perpendicular to the plane of projection of FIG. 5 and parallel to the longitudinal axis 19 of the shaft 13 of the medical resector 10. In both FIGS. 5 and 6, as in FIG. 4B, dimensions are provided by way of example.

Figure 7:
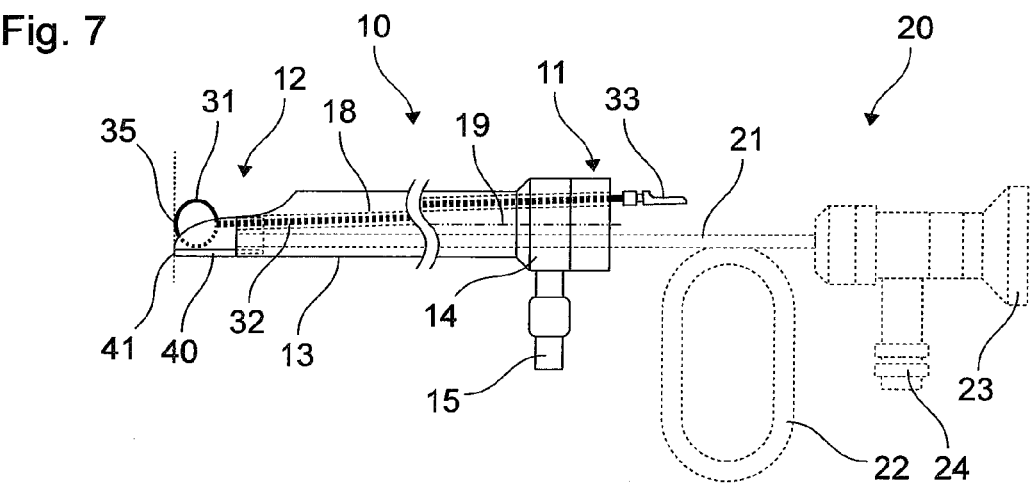
FIG. 7 shows a schematic depiction of an additional medical resector.

FIG. 7 shows a schematic view of an additional medical resector 10, which resembles in a few characteristics the medical resectors described above with reference to FIGS. 1 through 3. In particular, the medical resector 10 can be combined with an endoscope 20 that is indicated in FIG. 7 with broken lines. In addition the medical resector 10, similar as in the medical resector described above with reference to FIG. 1, comprises a rotatable HF electrode 31 whose distal end 35 terminates with the distal border 41 of a funnel collar 40 or is situated with this border in a plane perpendicular to the longitudinal axis 19 of the medical resector.

In a departure from the medical resectors described above with reference to FIGS. 1 through 3, in the medical resector 10 shown in FIG. 7 the funnel collar 40 is positioned in reverse, with reference to the axle 32, the connector 15, and other characteristics not symmetrical to the longitudinal axis 19. With reference to the non-symmetrical characteristics of the medical resector, the funnel collar 40 includes an area that is not included in the funnel collar of the medical resector shown in FIG. 1. Conversely, the funnel collar of the medical resector shown in FIG. 1 includes an area that is not included in the funnel collar 40.

Similarly as in the medical resectors described above with reference to FIGS. 1 through 3, the funnel collar 40 of the medical resector shown in FIG. 7 overlaps with the distal end of the shaft 13 or the wall that forms it. Departing from the medical resectors described above with reference to FIGS. 1 through 3, in the medical resector 10 shown in FIG. 7 the funnel collar 40 in the overlap area is not positioned outside the shaft 13 but rather inside or on the inner side of the wall of the shaft 13.

Figure 8:
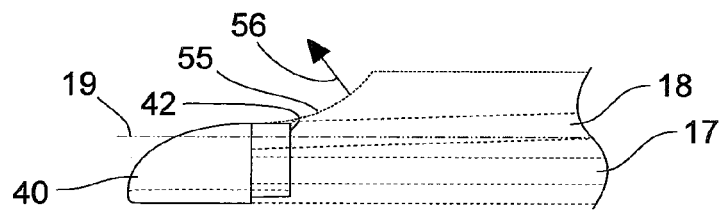
FIG. 8 shows an additional schematic depiction of the medical resector from FIG. 7.
Figure 9:
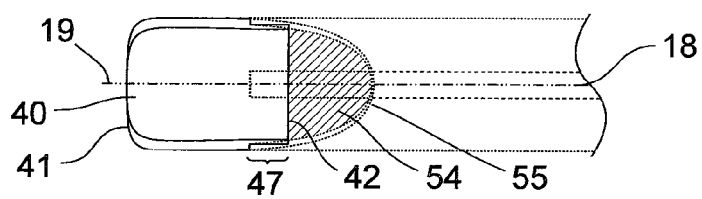
FIG. 9 shows an additional schematic depiction of the medical resector from FIG. 7.

In addition the resector 10 comprises a suction opening, which is described hereafter with reference to FIGS. 8 and 9. FIGS. 8 and 9 present schematically enlarged depictions of the distal end of the medical resector 10 described above with reference to FIG. 7. The plane of projection of FIG. 8 is parallel to the longitudinal axis 19 of the medical resector 10 and corresponds to the plane of projection of FIG. 7. The plane of projection of FIG. 9 is likewise parallel to the longitudinal axis 19 of the medical resector, but perpendicular to the planes of projection of FIGS. 7 and 8. To emphasize the shape of the funnel collar 40 more clearly, in FIGS. 8 and 9 the funnel collar 40 is drawn in solid lines and the contours of the shaft 13 of the medical resector 10 are indicated in finely broken lines. In addition the guide tube 17 for an endoscope and the guide tube 18 for the axle of the medical resector 10 are indicated in broken lines. The HF electrode and the axle of the medical resector 10 are not shown in FIGS. 8 and 9.

The overlapping of the funnel collar 40, more specifically the proximal end 42 of the funnel collar, and of the wall of the shaft 13 can be recognized in an area 47 in FIGS. 8 and 9. In area 47 the funnel collar 40 has a reduced wall thickness. The wall of the shaft 13 can also have a reduced wall thickness in area 47. In a departure from the depiction in FIGS. 7 through 9, only the wall of the shaft 13, or neither this wall nor the funnel collar 40, can have a reduced wall thickness in area 47. In area 47 the funnel collar 40 and the wall of the shaft 13 are connected, for instance by cementing.

On the distal end, the shaft 13 has a suction opening 54, which is shown with hatching for emphasis in FIG. 9. The suction opening 54 comprises an essentially D-shaped border 55, which includes one straight section and another that is essentially bow-shaped. The straight section of the border 55 is perpendicular to the longitudinal axis 19 of the medical resector 10. Corners between the straight section and the bow-shaped section of the border 55 of the suction opening 54 are positioned close to the border of the funnel collar 40.

Close to these corners, the bow-shaped section of the border 55 of the suction opening 54 is parallel or essentially parallel to the border of the funnel collar 40.

As already described in the foregoing, the area of the suction opening 54 refers to the surface bounded by the border 55 of the suction opening, and its entire interfaces with planes that are perpendicular to the longitudinal axis 19 of the medical resector 10 are straight. In the resector 10 described with reference to FIGS. 7 through 9, all local perpendicular lines 56 of the surface of the suction opening are parallel to the plane of projection of FIGS. 7 and 9. All local perpendicular lines 56 of the surface of the suction opening form angles with the longitudinal axis 19 of the medical resector 10 that are in the range of about 30 degrees to approximately 90 degrees. The central or centered perpendicular line of the surface of the suction opening forms an angle with the longitudinal axis 19 of the medical resector 10 that lies in the range from about 45 degrees to about 60 degrees.

What is claimed is:

1. A medical resector for ablating, cutting, or coagulating human or animal tissue, comprising:
   a shaft;
   a rotatable high-frequency electrode at a distal end of the shaft; and
   an axle, which runs from a proximal end to the distal end of the shaft and is mechanically coupled on the distal end with the high-frequency electrode;
   wherein the axle is positioned in the center or as close as possible to the center of a cross-section of the shaft at the distal end of the shaft and is positioned on the border or as close as possible to the border of the cross-section of the shaft at the proximal end of the shaft; and
   the axle has an axis of rotation that is non-parallel to a longitudinal axis of the shaft.

2. The medical resector according to claim 1, wherein the shaft has a circular cylindrical mantle surface, and the rotatable high-frequency electrode includes a wire sling whose center lies in or on an axis of symmetry of the mantle surface of the shaft.

3. The medical resector according to claim 1, further comprising:
   a guide tube in which the axle is positioned, so that the guide tube is positioned on the proximal end of the shaft on an outer wall of the shaft of the medical resector.

4. The medical resector according to claim 1, further comprising:
   a coupling device on the proximal end of the shaft for releasable mechanical coupling with a drive mechanism, which provides rotation frequencies in a rotation frequency range from 10 revolutions per minute to 200 revolutions per minute.

5. The medical resector according to claim 1, further comprising:
   a funnel collar for positioning on the distal end of the shaft of the medical resector, wherein the funnel collar is configured to surround partially the rotatable high-frequency electrode.

6. The medical resector according to claim 1, wherein the shaft of the medical resector has a cylindrical mantle, and the funnel collar has the shape of a section of the cylindrical mantle.

7. The medical resector according to claim 5, wherein the shaft of the medical resector has a mantle surface and the funnel collar is partly contiguous with the mantle surface.

8. The medical resector according to claim 5, wherein the funnel collar surrounds the high-frequency electrode at least halfway, with reference to the longitudinal axis of the shaft of the medical resector.

9. The medical resector according to claim 5, wherein the funnel collar surrounds the high-frequency electrode by at least three-quarters, with reference to the longitudinal axis of the shaft.

10. The medical resector according to claim 5, wherein a distal end of the high-frequency electrode extends beyond a distal border of the funnel collar.

11. The medical resector according to claim 5, wherein a distal border of the funnel collar ends flush with a distal end of the high-frequency electrode.

12. The medical resector according to claim 5, wherein a distal border of the funnel collar extends beyond a distal end of the high-frequency electrode.

13. The medical resector according to claim 5, further comprising:
   a suction opening on the distal end of the medical resector, wherein the suction opening is inclined with respect to the longitudinal axis of the medical resector.

14. The medical resector according to claim 5, further comprising:
   a suction opening on the distal end of the medical resector, wherein a section of a border of the suction opening forms a constant continuation of a section of a border of the funnel collar.

15. A medical resector for ablating, cutting, or coagulating human or animal tissue, comprising:
   a shaft;
   a rotatable high-frequency electrode at a distal end of the shaft;
   an axle, which runs from a proximal end to the distal end of the shaft and is mechanically coupled on the distal end with the high-frequency electrode; and
   a coupling device on the proximal end of the shaft for releasable mechanical coupling with a drive mechanism, which provides rotation frequencies in a rotation frequency range from 10 revolutions per minute to 200 revolutions per minute;
   wherein the axle is positioned in the center or as close as possible to the center of a cross-section of the shaft at the distal end of the shaft and is positioned on the border or as close as possible to the border of the cross-section of the shaft at the proximal end of the shaft.

16. A medical resector for ablating, cutting, or coagulating human or animal tissue, comprising:
   a shaft;
   a rotatable high-frequency electrode at a distal end of the shaft;
   an axle, which runs from a proximal end to the distal end of the shaft and is mechanically coupled on the distal end with the high-frequency electrode; and
   a funnel collar for positioning on the distal end of the shaft of the medical resector, wherein the funnel collar is configured to surround partially the rotatable high-frequency electrode;
   wherein the axle is positioned in the center or as close as possible to the center of a cross-section of the shaft at the distal end of the shaft and is positioned on the border or as close as possible to the border of the cross-section of the shaft at the proximal end of the shaft.

* * * * *